United States Patent [19]

Callery et al.

[11] 4,073,929

[45] Feb. 14, 1978

[54] 3-(2-SUBSTITUTED BENZIMIDAZOLYL) ALANINES

[75] Inventors: Patrick S. Callery, Cockeysville; Jeremy Wright, Baltimore; Nicolas Zenker, Lutherville, all of Md.

[73] Assignee: Merck & Co., Inc., Rahway, N.J.

[21] Appl. No.: 657,829

[22] Filed: Feb. 13, 1976

[51] Int. Cl.$^2$ ............... A61K 31/415; C07D 235/26
[52] U.S. Cl. ..................... 424/273 R; 260/518 R; 548/305; 548/329; 560/22
[58] Field of Search ............. 260/309.2; 424/273

[56] References Cited

PUBLICATIONS

English et al., Chem. Abst., 1945, vol. 39, cols. 1846–1847.
Jones et al., Chem. Abst., 1949, vol. 43, cols. 3362–3363.
Milkowski et al., J. Med. Chem., 1970, vol. 13, pp. 741–742.
Hofmann, Imidazole and its Derivatives, Part I, p. 288, N.Y., Interscience, 1953.
Zenker et al., J. Med. Chem., 1974, vol. 17, pp. 1223–1225.

*Primary Examiner*—Natalie Trousof
*Attorney, Agent, or Firm*—Daniel T. Szura; Donald J. Perrella

[57] ABSTRACT

Benzimidazol-5(6)-yl alanine derivatives useful as antihypertensive agents are disclosed as well as methods for their preparation.

10 Claims, No Drawings

3-(2-SUBSTITUTED BENZIMIDAZOLYL) ALANINES

BACKGROUND OF THE INVENTION

This invention relates to antihypertensive agents and to methods for their preparation and use. More particularly, it relates to antihypertensive agents comprising a 3-(2-substituted-benzimidazolyl)-alanine compound and to methods for the preparation and use of the antihypertensive agents.

DESCRIPTION OF THE PRIOR ART

The art records a long search for agents that are effective in treating hypertensive patients with acceptable clinical results and few, if any, side effects. There are, of course, a number of products available commercially which are useful for this purpose. One that has been extremely effective for the treatment of hypertension is the L form of 3-(3,4-dihydroxyphenyl)-2-methylalanine. This compound and its method of use is described in U.S. Pat. No. 3,344,023, issued in 1967. While a number of other compounds are well known in the art as antihypertensive drugs, the search continues for even more effective agents.

The compositions of the present invention are also alanine derivatives as are those described above, but are distinctly different from prior art compounds in that they contain a 3-(2-substituted)benzimidazolyl alanine.

OBJECTS OF THE INVENTION

It is, accordingly, an object of the present invention to provide new compounds that are useful as antihypertensive agents.

Another object is to provide antihypertensive agents that overcome or otherwise mitigate the problems of the prior art in this area.

A further object of the invention is to provide new benzimidazolone alanine compounds which exhibit antihypertensive activity as well as methods for the preparation of these new compounds.

Another object is to provide pharmaceutical compositions for administering these benzimidazolone alanine compounds.

A still further object of the invention is to provide methods for the treatment of subjects suffering from hypertension.

These and other objects and advantages of the present invention will become apparent from the following description.

SUMMARY OF THE INVENTION

In satisfaction of the foregoing objects and advantages, there are provided by this invention novel antihypertensive agents of the following general formula:

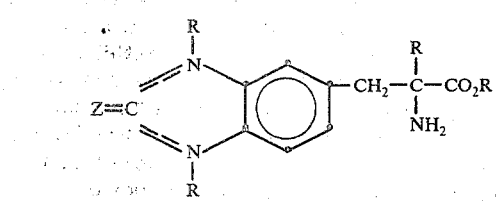

wherein Z is O= or RO—, and each R is hydrogen or alkyl of from 1 to about 3 carbon atoms. The foregoing general formula is intended to include the racemic mixtures, the D and L enantiomorphs, and the pharmaceutically acceptable carboxylic salts and acid-addition salts. Also provided are methods for the preparation of the compounds of the foregoing general formula, as well as pharmaceutical formulations, and methods for their use in the treatment of subjects suffering from hypertension to effect blood pressure lowering in these subjects.

DESCRIPTION OF PREFERRED EMBODIMENTS

As pointed out above, the invention is concerned with new antihypertensive agents which have been found to have outstanding antihypertensive activity and thus are extremely suitable for lowering the blood pressure of subjects suffering from hypertension. The antihypertensive agents may be best described as comprising a compound of the following general structural formula

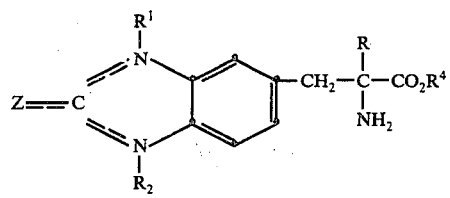

wherein Z is O= or RO—, each R, $R^1$, $R^2$, $R^3$ and $R^4$ is hydrogen or alkyl of from 1 to about 3 carbon atoms but preferably methyl. It is to be understood that the present invention is directed to not only the racemmic mixtures but also the D and L enantiomorphs. Also the invention is inclusive of the pharmacologically acceptable carboxylic salts, e.g. Na, K or Ca and the pharmacologically acceptable acid-addition salts formed with pharmaceutically acceptable acids.

The compounds of formula I include oxo compounds of formula II

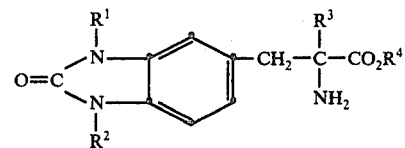

as well as ether compounds of formula IVa and IVb:

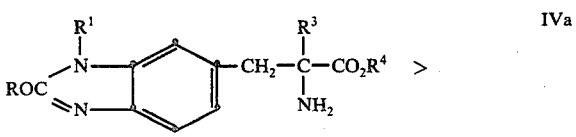

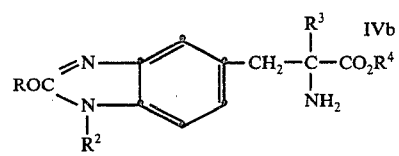

It will be understood by those skilled in the art that the compound of the foregoing general formula II wherein Z is O= and $R^2$ or R' is hydrogen exists in a tautomeric equilibrium with the corresponding 2-hydroxy-benzimidazoles:

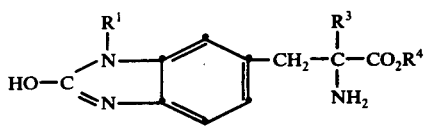 IIIa

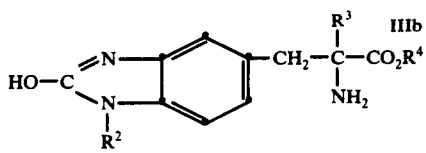 IIIb

The compounds of the foregoing general formula IVa and IVb wherein Z is RO— are alkyl ethers of the 2-hydroxy tautomers of formula IIIa and IIIb.

Specific compounds of the present invention include the following:

3-(Benzimidazol-2-one-5-yl)-alanine;
3-(Benzimidazol-2-one-5-yl)-2-methylalanine;
2-Amino-3-(3-methyl-2-oxo-1H-benzimidazol-5-yl)-propionic acid;
2-Amino-2-methyl-3-(3-methyl-2-oxo-1H-benzimidazol-5-yl)-propionic acid;
2-Amino-3-(3-methyl-2-oxo-1H-benzimidazol-6-yl)-propionic acid;
2-Amino-2-methyl-3-(3-methyl-2-oxo-1H-benzimidazol-6-yl)-propionic acid;
2-Amino-3-(1,3-dimethyl-2-oxo-2H-benzimidazol-5-yl)-propionic acid;
2-Amino-2-methyl-3-(1,3-dimethyl-2-oxo-2H-benzimidazol-5-yl)-propionic acid;
2-Amino-3-(2-ethoxybenzimidazol-5-yl)propionic acid;
2-Amino-3-(1-methyl-2-ethoxybenzimidazol-6-yl)propionic acid;
2-Amino-3-(1-methyl-2-ethoxybenzimidazol-5-yl)propionic acid;
2-Amino-2-methyl-3-(2-ethoxybenzimidazol-5-yl)propionic acid;
2-Amino-2-methyl-3-(1-methyl-2-ethoxybenzimidazol-5-yl)propionic acid;
2-Amino-2-methyl-3-(1-methyl-2-ethoxybenzimidazol-6-yl)propionic acid; and
D,L-3-(Benzimidazol-2-one-5-yl)-2-methylalanine methyl ester The compounds of the present invention of formulas I and II may be prepared by the reaction of phosgene with a diamino compound of the formula

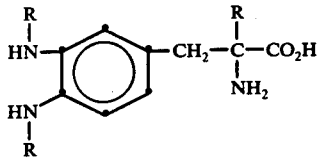 V wherein R is hydrogen or alkyl of from 1 to about 3 carbon atoms.

This reaction takes place under conventional conditions at temperatures of from about 10° C. to about 30° C., preferably at about room temperature, over a period of from a few minutes to several hours, preferably for about 0.5 to about 2 hours.

The diamino compound of formula V may be prepared by hydrogenating a compound of the formula

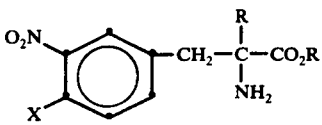 VI wherein X is nitro or amino. The hydrogenation preferably is carried out catalytically under conventional conditions, by using a palladium/carbon catalyst at about room temperature at a pressure of about 2.5 atmospheres.

The alkyl ethers of formula IV may be prepared by reacting a diamino compound of formula V with iminocarbonic acid diethylester following the procedure of Sandmeyer, Ber., 19, 2650 (1886) which disclosure is hereby incorporated by reference.

The final compounds of the present invention have been found to be effective in reducing elevated blood pressure in mammalian species, e.g. rats, and so are useful as antihypertensive agents. The compounds may be administered either orally or parenterally and they can be compounded by the usual pharmaceutical methods for use in the lowering of blood pressure in subjects suffering from hypertension. Dosage units for the compounds may vary from about 0.05 to about 100 mg per kg per day. Normal dosage units for the compounds for oral administration will vary from about 10 to about 500 mg per kg per day. For oral administration to humans the dosage range is from about 0.1 to about 5 grams per day, preferably from about 0.5 to about 1.5 grams per day, usually in small but frequent doses, e.g. in from 1 to 4 doses per day.

The antihypertensive agents of the present invention in the described dosages may be administered orally, however, other routes such as intraperitoneally, subcutaneously, intramuscularly or intravenously, may be employed.

For oral therapeutic administration, the active compounds of this invention may be incorporated with excipients and used in the form of tablets, troches, capsules, elixirs, suspensions, syrups, wafers, chewing gums, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; and excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as hydrochloric, hydrobromic, sulfuric, and phosphoric acids, and organic acids such as maleic, fumaric, tartaric, citric, 2-acetoxybenzoic, salicylic, succinic, or methanesulfonic acids.

The following examples illustrate the present invention without, however, limiting the same thereto. All temperatures are expressed in degrees Celsius.

EXAMPLE 1

DL-3-(Benzimidazol-2-one-5-yl)-2-methylalanine Hydrochloride

A mixture of DL-methyl N-acetyl-3-(3-nitro-4-acetamidophenyl)-2-methylalanate (0.85 g., 2.5 mmole) and 4N HCl (50 ml.) is held at reflux for 2 hours. The resulting red-orange solution is cooled and then reduced with hydrogen (initial pressure 35 psi) on 10% palladium on charcoal catalyst (300 mg.) at room temperature overnight. The mixture is then filtered under a nitrogen atmosphere through a bed of diatomaceous earth by suction and phosgene is bubbled (approximately 60 ml/min.) through the filtrate for 1 hour. The white precipitate which develops is collected: 0.4 g., 1.5 mmole, 59%. Two recrystallizations from $H_2O$ provide an analytical sample; m.p. 333° (decomp).

EXAMPLE 2

L-3-(Benzimidazol-2-one-5-yl)-2-methylalanine Hydrochloride

Following the procedure for the production of the racemic mixture in Example 1, L-methyl N-acetyl-3-(3-nitro-4-acetamidophenyl)-2-methylalanate is hydrolyzed and then cyclized with phosgene to give the title compound: m.p. 303° (decomp).

EXAMPLE 3

DL-3-(Benzimidazol-2-one-5-yl)alanine Hydrochloride

Following the procedure for the production of the racemic mixture in Example 1, diethyl 2-(3-nitro-4-acetamidobenzyl)-2-acetamidomalonate is hydrolyzed and cyclized with phosgene to yield the pure title compound in 54% yield: m.p. 259° (decomp).

EXAMPLE 4

2-Amino-3-(3-methyl-2-oxo-1H-benzimidazol-5-yl)propionic Acid Hydrochloride

A.

Diethyl-2-(3-nitro-4-acetamidobenzyl)-2-acetamidomalonate

A mixture of diethyl-4-aminobenzylacetamidomalonate (85 g., 0.254 M), glacial acetic acid (85 ml.) acetic anhydride (85 ml.), and zinc dust (2.2 g.) is refluxed for 30 minutes. While still hot, the mixture is poured into stirred ice water. The resulting precipitate is filtered, washed with water and recrystallized from ethanol:water to yield 91.2 g. (96%) of diethyl-4-acetylaminobenzylacetamidomalonate, m.p. 173°-174°.

To a mixture of diethyl-4-acetylaminobenzylacetamidomalonate (15 g., 0.04 M) suspended in acetic anhydride (49 ml.) 70% nitric acid (17 ml.) is added slowly with stirring while maintaining the reaction temperature at 35°-40°. After the addition is complete, the yellow solution is maintained at 40° for 2 hours, then poured into 600 ml. of stirred ice water. The resulting precipitate is filtered rapidly and washed with water. Recrystallization from ethanol:water yields 14.4 g (85%) of diethyl-2-(3-nitro-4-acetamidobenzyl)-2-acetamidomalonate, m.p. 172°-172.5°.

B.

2-Amino-3-(3-methyl-2-oxo-1H-benzimidazol-5-yl)propionic Acid Hydrochloride

The title compound is prepared by treating the product from part A with 4N HCl at reflux for 2 hours, evaporation of the volatile solvents and treating the residue with hydrogen, formaldehyde, sodium acetate and Raney nickel catalyst according to the procedure of Emerson et al., J. Am. Chem. Soc. 62, 69 (1940). Phosgene gas is then bubbled (approximately 60 ml/min) through the resulting mixture in 1N HCl (100 ml) for 1 hour to yield the title compound.

EXAMPLE 5

2-Amino-3-(1,3-dimethyl-2-oxo-2H-benzimidazol-5-yl)propionic Acid Hydrochloride

A.

Diethyl-2-(3-nitro-4-N-methylacetamidobenzyl)-2-acetamidomalonate

Diethyl 4-nitrobenzylacetamidomalonate (10 g.) is treated with hydrogen, formaldehyde, sodium acetate and Raney nickel catalyst by the procedure of part B of Example 4 to produce the 4-methylamino product which is refluxed for one hour with a slight excess of acetyl chloride to produce the N-methyl-4-acetamido product. The latter product is added slowly to 20 ml of stirring $HNO_3$ (red, fuming) at −15°. After stirring, the mixture is added to an ice cold saturated $NaHCO_3$ solution, and the resulting precipitate is filtered and crystallized twice from benzene.

B.

2-Amino-3-(1,3-dimethyl-2-oxo-2H-benzimidazol-5-yl)propionic Acid Hydrochloride

The title compound is prepared by treating the product from part A first with hydrogen, formaldehyde, sodium acetate and Raney nickel catalyst according to the procedure of Example 4, secondly with 10% hydrochloric acid heated to reflux for 1 hour and finally with phosgene gas for 1 hour by the procedure of part B of Example 4.

EXAMPLE 6

2-Amino-3-(3-methyl-2-oxo-1H-benzimidazol-6-yl)propionic Acid Hydrochloride

By following the procedure of Example 1 but substituting diethyl-2-(3-nitro-4-N-methylacetamidobenzyl)-2-acetamidomalonate (prepared as described in part A of Example 5) for DL-methyl-N-acetyl-3-(3-nitro-4-acetamidophenyl)-2-methylalanate, the title compound is prepared.

EXAMPLE 7

2-Amino-2-methyl-3-(3-methyl-2-oxo-1H-benzimidazol-6-yl)propionic Acid Hydrochloride

A. Methyl 2-acetamido-2-methyl-3-(3-nitro-4-N-methylacetamidophenyl)propionate Methyl 2-acetamido-2-methyl-3-(4-nitrophenyl)propionate is treated with hydrogen, formaldehyde, sodium acetate and Raney nickel catalyst by the procedure of part B of Example 4 to produce the crude 4-methylamino product which when treated with a slight excess of acetic anhydride and heated to reflux for 1 hour, yields the 4-N-methylacetamido compound. The latter product is added slowly to 20 ml of stirring HNO₃ (red fuming) at −15°. After stirring, the mixture is added to an ice cold saturated NaHCO₃ solution, and the resulting precipitate is filtered and recrystallized twice from benzene.

B.
2-Amino-2-methyl-3-(3-methyl-2-oxo-1H-benzimidazol-6-yl)propionic Acid Hydrochloride The title compound is prepared by treating the product from part A with 10% hydrochloric acid heated to reflux for 1 hour followed by reaction with hydrogen gas over palladium on carbon, and treating the resulting mixture with phosgene gas by the method of part B of Example 4.

EXAMPLE 8

2-Amino-2-methyl-3-(3-methyl-2-oxo-1H-benzimidazol-5-yl)propionic Acid Hydrochloride Methyl 2-acetamido-2-methyl-3-(3-nitro-4-acetamidophenyl)propionate is treated with hydrogen, formaldehyde, sodium acetate and Raney nickel following the procedure of part B of Example 4 to produce 2-acetamido-2-methyl-3(3-methylamino-4-aminophenyl)propionic acid. This product is hydrolyzed with 10% HCl and cyclized with phosgene by the procedure of part B of Example 4 to yield the title compound.

EXAMPLE 9

2-Amino-2-methyl-3-(1,3-dimethyl-2-oxo-2H-benzimidazol-5-yl)propionic Acid Hydrochloride Following the procedure of Example 8 but replacing the product of part A, Example 7 for methyl-2-acetamido-2-methyl-3-(3-nitro-4-acetamidophenyl)propionate, the title compound is prepared.

EXAMPLE 10

2-Amino-3-(2-ethoxybenzimidazol-5-yl)propionic Acid

A mixture of diethyl-2-(3-nitro-4-acetamidobenzyl)-2-acetamidomalonate is held at reflux with 10% HCl for 2 hours. The resulting mixture is cooled and then treated with hydrogen (initial pressure 35 psig) on 10% palladium on charcoal catalyst at room temperature overnight. The solution is then evaporated to dryness and the residue treated with a slight excess of iminocarbonic acid diethylester following the procedure of Sandmeyer [Ber., 19, 2650 (1886)] to give the title compound.

EXAMPLE 11

2-Amino-3-(1-methyl-2-ethoxybenzimidazol-6-yl)propionic Acid

The title compound is prepared by treating the product from part A of Example 4 with hydrogen, formaldehyde, sodium acetate and Raney nickel catalyst according to the procedure of part B of Example 4 and then treating the resulting mixture with 10% HCl held at reflux for 2 hours followed by evaporation to dryness and treatment of the residue with iminocarbonic acid diethyl ester by the procedure of Example 10.

EXAMPLE 12

2-Amino-3-(1-methyl-2-ethoxybenzimidazol-5-yl)propionic Acid

By following the procedure of Example 10 but substituting diethyl-2-(3-nitro-4-N-methylacetamidobenzyl)-2-acetamidomalonate (Example 5, part A) for diethyl-2-(3-nitro-4-acetamidobenzyl)-2-acetamidomalonate, the title compound is prepared.

EXAMPLE 13

2-Amino-2-methyl-3-(2-ethoxybenzimidazol-5-yl)propionic Acid

By following the procedure of Example 10 but substituting methyl-2-acetamido-2-methyl-3-(3-nitro-4-acetamidophenyl)propionate for diethyl-2-(3-nitro-4-acetamidobenzyl)-2-acetamidomalonate, the title compound is prepared.

EXAMPLE 14

2-Amino-2-methyl-3-(1-methyl-2-ethoxybenzimidazol-5-yl)propionic Acid

By following the procedure of Example 10 but substituting methyl-2-acetamido-2-methyl-3-(3-nitro-4-N-methylacetamidophenyl)propionate (Example 7, part A) for diethyl-2-(3-nitro-4-acetamidobenzyl)-2-acetamidomalonate, the title compound is prepared.

EXAMPLE 15

2-Amino-2-methyl-3-(1-methyl-2-ethoxybenzimidazol-6-yl)propionic Acid

Methyl-2-acetamido-2-methyl-3-(3-nitro-4-acetamidophenyl)propionate is treated with hydrogen, formaldehyde, sodium acetate and Raney nickel following the procedure of Example 4 to produce the 3-methylamino product. The title compound is prepared by following the procedure of Example 11 but substituting the 3-methylamino product [methyl-2-acetamido-2-methyl-3-(3-methylamino-4-acetamidophenyl)propionate] for methyl-2-(3-methylamino-4-acetamidobenzyl)-2-acetamidomalonate.

EXAMPLE 16

D,L-3-(Benzimidazol-2-one-5-yl)-2-methylalanine methyl ester

A mixture of the product of Example 1 (0.1 mole) is held at reflux in 1500 ml of MeOH saturated with HCl gas for 6 hours. The alcoholic solution is evaporated to yield a gum which is recrystallized from water or MeOH:ether.

EXAMPLE 17

PREPARATION OF CAPSULE FORMULATION

| Ingredient | Milligrams per Capsule |
|---|---|
| L-3-(Benzimidazol-2-one-5-yl)-2-methyl alanine hydrochloride | 400 |
| Starch | 80 |
| Magnesium stearate | 5 |

The active ingredient, starch and magnesium stearate are blended together. The mixture is used to fill hard shell capsules of a suitable size at a full weight of 485 milligrams per capsule.

EXAMPLE 18

PREPARATION OF TABLET FORMULATION

| Ingredient | Milligrams per Tablet |
|---|---|
| Dl-3-(Benzimidazol-2-one-5-yl) alanine hydrochloride | 100 |
| Lactose | 200 |
| Corn starch (for mix) | 50 |
| Corn starch (for paste) | 50 |
| Magnesium stearate | 6 |

The active ingredient, lactose and corn starch (for mix), are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 100 milligrams of active ingredient.

EXAMPLE 19

PREPARATION OF ORAL SYRUP FORMULATION

| Ingredient | Amount |
|---|---|
| 2-Amino-3-(3-methyl-2-oxo-1H-benzimidazol-5-yl)-propionic acid hydrochloride | 90 mg |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water qs to | 100 ml. |

The sorbitol solution is added to 40 milliliters of water and the active ingredient is supended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

EXAMPLE 20

To demonstrate the antihypertensive effect of representative compounds of the present invention, arterial pressure is recorded in conscious spontaneously hypertensive male rats of the Wistar-Okamoto strain obtained from Carworth Farms (Vincentown, N.J.). The animals are of 300–500 g. body weight. To record arterial pressure, the caudal artery is cannulated; pressure is recorded continuously on a Honeywell 906C Visicorder. 3-(Benzimidazol-2-one-5-yl)alanine hydrochloride shows antihypertensive activity at 80 mg/kg i.p. while 3-(benzamidazol-2-one-5-yl)-2-methylalanine hydrochloride shows antihypertensive activity at 20 mg/kg i.p.

What is claimed is:

1. A compound of the formula

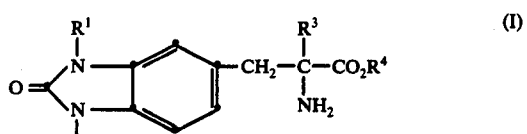

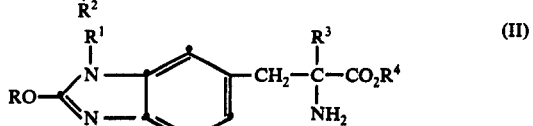

or

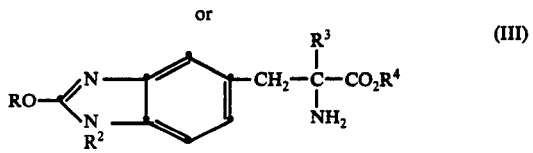

wherein each of R, $R^1$, $R^2$, $R^3$ and $R^4$ is hydrogen or alkyl of from 1 to about 3 carbon atoms, and the pharmaceutically acceptable carboxylic salts and pharmaceutically acceptable acid-addition salts thereof.

2. A compound according to claim 1 having formula I.

3. A compound according to claim 1 having formula II or III.

4. A compound according to claim 1 wherein each of $R^1$, $R^2$, $R^3$ and $R^4$ is hydrogen or methyl.

5. A compound according to claim 2 wherein each of $R^1$, $R^2$, $R^3$ and $R^4$ is hydrogen or methyl.

6. A compound according to claim 3 wherein each of $R^1$, $R^2$, $R^3$ and $R^4$ is hydrogen or methyl.

7. A compound according to claim 1 wherein $R^3$ is methyl.

8. A compound according to claim 1 wherein $R^1$ and $R^2$ are each hydrogen.

9. A method for the treatment of hypertension in a mammalian species which comprises administering to a hypertensive subject an effective amount of a compound of claim 1.

10. A composition useful for treating hypertension comprising a compound of claim 1 in combination with a pharmaceutically acceptable carrier.

* * * * *